(12) United States Patent
Blanche et al.

(10) Patent No.: US 7,202,078 B2
(45) Date of Patent: *Apr. 10, 2007

(54) COMPOSITION INTENDED FOR THE PRESERVATION OF INFECTIOUS RECOMBINANT ADENOVIRUSES

(75) Inventors: Francis Blanche, Paris (FR); Shian-Jiun Shih, Foster City, CA (US)

(73) Assignee: Centelion (FR)

( * ) Notice: Subject to any disclaimer, the term of this patent is extended or adjusted under 35 U.S.C. 154(b) by 176 days.

This patent is subject to a terminal disclaimer.

(21) Appl. No.: 10/812,912

(22) Filed: Mar. 31, 2004

(65) Prior Publication Data

US 2004/0191909 A1 Sep. 30, 2004

Related U.S. Application Data

(63) Continuation of application No. 09/970,663, filed on Oct. 5, 2001, now Pat. No. 6,734,008, which is a continuation of application No. PCT/FR00/00879, filed on Apr. 7, 2000.

(60) Provisional application No. 60/132,120, filed on Apr. 30, 1999.

(30) Foreign Application Priority Data

Apr. 9, 1999 (FR) .................................. 99 04443

(51) Int. Cl.
*C12N 15/00* (2006.01)
(52) U.S. Cl. .................................. 435/320.1
(58) Field of Classification Search .............. 435/320.1
See application file for complete search history.

(56) References Cited

U.S. PATENT DOCUMENTS

| 5,871,464 A | * | 2/1999 | Tryggvason et al. | ........ 604/506 |
| 6,451,256 B1 | * | 9/2002 | Sene | ........................... 422/40 |
| 6,734,008 B2 | * | 5/2004 | Blanche et al. | .......... 435/235.1 |
| 2002/0031527 A1 | * | 3/2002 | Wu et al. | ................ 424/233.1 |

FOREIGN PATENT DOCUMENTS

WO  WO 98/02522  * 1/1998

OTHER PUBLICATIONS

U.S. Appl. No. 60/133,116, filed May 7, 1999, Wu et al.*
U.S. Appl. No. 60/108,606, filed Nov. 16, 1999, Wu et al.*
Amin, R., et al., "Replication-Deficient Adenovirus Induces Expression of Interleukin-8 by Airway Epithelial Cells *In Vitro*," Human Gene Therapy, 6:145-153 (1995).

Bajocchi, G., et al., "Direct *In Vivo* Gene Transfer to Ependymal Cells in the Central Nervous System Using Recombinant Adenovirus Vectors," Nature Genetics, 3:229-234, (1993).

Colak, A., et al., "Adenovirus-Mediated Gene Therapy in an Experimental Model of Breast Cancer Metastatic to the Brain," Human Gene Therapy, 6:1317-1322 (1995).

Crystal, R.G., et al., "A Phase 1 Study, in Cystic Fibrosis Patients, of the Safety, Toxicity, and Biological Efficacy of a Single Administration of a Replication Deficient, Recombinant Adenovirus Carrying the cDNA of the Normal Cystic Fibrosis Transmembrane Conductance Regulator Gene in the Lung," Human Gene Therapy, 6:643-666 (1995).

Fang, B., et al., "Gene Therapy for Hemophilia B: Host Immunosuppression Prolongs the Therapeutic Effect of Adenovirus-Mediated Factor IX Expression," Human Gene Therapy, 6:1039-1044 (1995).

Kagami, H., et al., "Evidence for the Systemic Delivery of a Transgene Product from Salivary Glands," Human Gene Therapy, 7:2177-2184 (1996).

Korst, R.J., et al., "*In Vitro* and *In Vivo* Transfer and Expression of Human Surfactant SP-A- and SP-B-Associated Protein cDNAs Mediated by Replication-Deficient, Recombinant Adenoviral Vectors," Human Gene Therapy, 6:277-287 (1995).

Lieber, A., et al., "Adenovirus-Mediated Transfer of the Amphotropic Retrovirus Receptor cDNA Increases Retroviral Transduction in Cultured Cells," Human Gene Therapy, 6:5-11 (1995).

Mittereder, N., et al., "Evaluation of the Concentration and Bioactivity of Adenovirus Vectors for Gene Therapy," Journal of Virology, 70:7498-7509 (1996).

Rosenfeld, M.A., et al., "*In Vivo* Transfer of the Human Cystic Fibrosis Transmembrane Conductance Regular Gene to the Airway Epithelium," Cell, 68:143-155 (1992).

Sene, C., et al., "Aerosol-Mediated Delivery of Recombinant Adenovirus to the Airways of Nonhuman Primates," Human Gene Therapy, 6:1587-1593 (1995).

Von Seggern, D.J., et al., "A Helper-Independent Adenovirus Vector with E1, E2, and Fiber Deleted: Structure and Infectivity of Fiberless Particles," Journal of Virology, 73:1601-1608 (1999).

Vrancken Peeters, M-J, et al., "Adenovirus-Mediated Hepatic Gene Transfer in Mice: Comparison of Intravascular and Biliary Administration," Human Gene Therapy, 7:1693-1699 (1996).

* cited by examiner

*Primary Examiner*—Brian Whiteman
(74) *Attorney, Agent, or Firm*—Finnegan, Henderson, Farabow, Garrett & Dunner, LLP

(57) ABSTRACT

Liquid or frozen compositions containing adenoviral-particles, comprising a buffer solution capable of maintaining the pH of the medium at slightly alkaline values, supplemented with glycerol and without addition of divalent metal cations or of alkali metal cations.

10 Claims, No Drawings

COMPOSITION INTENDED FOR THE PRESERVATION OF INFECTIOUS RECOMBINANT ADENOVIRUSES

This application is a continuation of U.S. patent application Ser. No. 09/970,663, filed on Oct. 5, 2001, issued on May 11, 2004, as U.S. Pat. No. 6,734,008, which is a continuation of PCT/FR00/00879 filed on Apr. 7, 2000, and claims benefit of priority of U.S. provisional application No. 60/132,120, filed Apr. 30, 1999, and French application 99/04443, filed Apr. 9, 1999, each of which is incorporated by reference herein.

The present invention relates to the preservation of adenoviruses in a stabilized and storable form and to the liquid or frozen compositions intended for this preservation.

The preservation of adenoviruses in stable compositions is a known problem, which has been the subject of many studies, without as a result giving truly satisfactory results up until now. Recombinant viruses can in fact be used only if they can be stored successfully without degradation and without loss of their infectivity.

The physical state of the adenoviral particles, in solution, undergoes two types of impairments simultaneously and rapidly over time on the one hand, aggregation (coagulation) of the particles in the form of lumps or filaments, which is an extremely serious phenomenon because it is irreversible, and, on the other hand, disintegration of the icosahedral structure of the capsids themselves (by lysis of the capsids and release of the capsomers into the medium).

In International Application WO 98/02522, there has been described a method of preserving infectious recombinant viruses in the form of a suspension in an aqueous solution comprising sucrose. The recommended compositions do not contain glycerol and contain, according to a preferred aspect, at least one divalent cation or monovalent alkali metal cation salt.

However, it can be shown that sucrose does not systematically provide stabilization at +4° C., and depending on the cases, stabilization at this temperature never exceeds a period of 2 weeks, or is at best less than 2 months.

In J. Virology, 70(11), 7498–7509 (1996), there have been described adenovirus preservations in the form of buffer solutions based on Tris buffer and glycerol, but systematically containing magnesium chloride. These preparations require preservation at very low temperatures, of the order of –70° C. to avoid a reduction in their infectivity.

In Human Gene Therapy, 7, 1693–99 (1996), there is also used a formulation for storage based on Tris buffer and glycerol, and comprising magnesium chloride. This formulation is preserved at –80° C.

More generally, the Tris-based formulations described in the literature up until now systematically contain magnesium chloride (1 mM in general) and/or a salt at physiological concentration (generally NaCl at 150 mM). There may be mentioned, for example by way of illustration, [Cell, 68, 143–155 (1992); Nature Genetics, 3, 229–234 (1993); Human Gene Therapy, 6, 5–11 (1995); Human Gene Therapy, 6, 145–153 (1995); Human Gene Therapy, 6, 277–287 (1995); Human Gene Therapy, 6, 643–666 (1995); Human Gene Therapy, 6, 1039–1044 (1995); Human Gene Therapy, 6, 1317–1322 (1995); Human Gene Therapy, 6, 1587–1593 (1995); Human Gene Therapy, 7, 2177–2184 (1996); J. Virology, 73, 1601–1608 (1999)]. When specified by the authors, the preservation of the virus is systematically carried out at –70° C./–80° C.

It has since been shown that the variation in the viral structure (aggregation and lysis) is a phenomenon which is highly dependent on factors such as the concentration of certain cationic counterions added to the solution and also such as the adenovirus concentration. Above concentrations of about 1E12 vp/ml, the aggregation and disintegration of the capsids (and therefore the loss of infectivity) are observed within a few hours to a few days, depending on the pharmaceutical compositions used, whereas these phenomena become slower at low concentration. Because of this, it is particularly difficult to preserve for a prolonged period compositions with high concentrations of viral particles.

It has thus been found, and this is what constitutes the subject of the present invention, that infectious recombinant adenoviruses could be preserved in aqueous medium, at temperatures of between +4 and +20° C., in the form of a suspension in a buffer solution capable of maintaining the pH of the medium at slightly alkaline vales, supplemented with glycerol and without addition of divalent metal cations or of alkali metal cations.

More specifically, the pH of the medium is maintained between 8.0 and 9.6.

The liquid or frozen compositions containing the adenoviral particles in a buffer solution supplemented with glycerol also fall within the scope of the present invention. These compositions have the considerable advantage of a good stability, but also of being particularly suited to the preservation of high concentrations of viral particles for a prolonged period.

According to the invention, the buffer solution capable of maintaining the pH of the medium between 8.0.and 9.6 consists either of an acid/base system comprising Tris [tris (hydroxymethyl)-aminomethane], or lysine and an acid chosen from a strong acid (hydrochloric acid for example) or a weak acid (maleic acid, malic acid or acetic acid for example), or of an acid/base system comprising Hepes [2-(4-(2-hydroxyethylpiperazin)-1-yl)ethanesulphonic acid] and a strong base (sodium hydroxide for example).

Preferably, the pH is maintained between 8.4 and 8.8 and still more particularly at 8.4 (value measured at 25° C.).

The concentration of the buffer solution is determined so as to exert the buffering effect within a limit and in a volume where the pH value is not affected. The molar concentration of acid+base may vary from 10 to 500 mM, preferably from 20 to 100 mM, and more particularly it is maintained at 20 mM. Among the buffer systems according to the invention, the Tris/HCl buffer solution at a concentration of 20 mM gives particularly satisfactory results.

According to the invention, the composition contains 10 to 50% glycerol, and preferably between 20 and 25% (volume for volume).

The compositions according to the invention may, in addition, optionally contain other adjuvants. The latter may be chosen from polymers (polyethylene glycols, for example PEG 400, PEG 8000), the pluronics (Pluronic F68 for example), in particular in an amount of about 1 to 20% by weight, the polysorbates (in particular Tween-20, for example at 0.01 to 1% by weight), or chosen from sugars such as for example sucrose, mannitol or dextrose (in particular in an amount of about 5 to 10%) or alternatively from alcohols (in particular ethanol) in an amount of 1 to 10% by volume.

The compositions according to the invention are particularly suited to the preservation of adenoviral preparations of high concentration. Indeed, the compositions thus stabilized make it possible to maintain the viral particles in a liquid aqueous suspension (in particular between +4 and +20° C.) while preserving the infectivity of the virus, this being given at very high viral concentrations (from values of 1E8 vp/ml up to 1E12 vp/ml or up to 1E13 vp/ml and which may even be as high as 5E13 vp/ml).

According to another alternative of the invention, the virus may also be frozen at −20° C., thus preserved for several months or for a longer period, and then thawed in this formulation with no harm either to its structure or its infectivity.

According to the invention, the compositions may be prepared by suspending, in the buffer solution, adenoviral particles initially obtained in aqueous solution, and then purified, followed by the addition of glycerol and optionally by the addition of an adjuvant as cited above.

The infectious recombinant adenovirus may be obtained according to the usual methods of production in cells of encapsidation transcomplementing lines, for example the cells of the 293 line or of the PER-C6 line. The viral particles may then be purified by caesium chloride gradient centrifugation as described, for example, in Journal of General Virology, 34, 19–35 (1977). More preferably, the viral particles are purified by liquid chromatography in anion-exchange mode, gel filtration, in hydrophobic mode or by metal chelation. The purification by anion exchange is particularly advantageous since it makes it possible to obtain, in a single chromatographic step, a pure viral preparation, free of the proteins, the nucleic acids and other impurities and metabolites obtained from the producing cell, and free of the compounds brought by the culture medium. Preferred modes of purification by chromatography are described in International Application WO 98/00524 or as below in the examples. The adenoviral particles are then formulated in the preservation buffer selected using in particular dialysis, diafiltration or gel filtration chromatography methods. The composition thus obtained may be optionally frozen and preserved at a desired. storage temperature (for example −20° C.), but this operation is, however, not essential for preservation over a long period, the compositions being stable in the liquid state between +4 and +20° C.

The compositions according to the invention are stable, without notable degradation [physical and biological stability (infectivity)] for a period of at least 6 months at +4° C. and of at least 5 months at +20° C. Physically stable solution is more particularly understood to mean a solution which does not exhibit the appearance of coagulation, of sedimentation of particles or of precipitate (by visual estimation, by measurement of the optical density, by electron microscopy analysis, or by analysis of the size distribution of the particles) after the period of preservation considered.

The present invention relates more particularly to the preservation of infectious adenoviruses in a stabilized form and to the liquid or frozen compositions intended for this preservation.

The formulation according to the invention is of interest in that it is the first composition made which allows the preservation of adenoviruses in liquid form at temperatures of +4 to +20° C. while having the possibility of having a high viral concentration. The invention is particularly advantageous in its application to recombinant adenoviruses, but it can be applied in general to all adenoviruses (wild-type or recombinant).

By way of example, there may be mentioned in particular the adenoviruses below which may be advantageously preserved in a composition according to the invention: all the human wild-type adenoviruses, belonging to the six known subgroups called A, B, C, D, E and F, and more particularly all 49 different serotypes of human adenoviruses constituting these six subgroups. Likewise, the invention may be applied to simian, bovine, equine, porcine, ovine or canine wild-type viruses belonging to the Adenoviridae family. Furthermore, the invention may be applied to the mutant viruses obtained from the wild-type viruses belonging to the Adenoviridae family.

Among the recombinant adenovirus vectors to which the present invention may be applied, there may be mentioned all the modified adenoviruses containing one or more deletions in the region of the genome called E1, or in the E2 region, or in the E3 region or in the E4 region, as well as the recombinant viruses containing several deletions combined in the above regions, as well as the completely deleted recombinant viruses (called gutless) [FASEB, 11, 615 (1997)].

Likewise, the present invention also applies to the recombinant adenoviral vectors containing, in addition, a nucleic acid of interest. The nucleic acid of interest may be inserted at different sites of the adenovirus genome. Advantageously, it is inserted at the level of the E1, E3 or E4 region. However, it is clear that other sites may be used. In particular, access to the nucleotide sequence of the genome allows persons skilled in the art to identify regions which make it possible to insert the nucleic acid of interest. The nucleic acid of interest may be any DNA sequence introduced, in particular any sequence whose transfer and/or expression in the target cell is sought.

In particular, it may contain one or more therapeutic genes and/or one or more genes encoding antigenic proteins. The therapeutic genes which may thus be transferred are all the genes whose transcription and optionally translation in the target cell generate products having a therapeutic effect. Among the therapeutic products, there may be mentioned more particularly enzymes, blood derivatives, hormones, lymphokines: interleukins, interferons, TNF and the like (WO93/19191), growth factors, neurotransmitters or precursors thereof or synthesis enzymes, trophic factors: BDNF, CNTF, NGF, IGF,.GMF, aFGF, bFGF, NT3, NT5 and the like, apolipoproteins: ApoAI, ApoIV, ApoE, and the like (WO94/25073), dystrophin or a minidystrophin (WO93/06223), the genes which make it possible to control restenosis: GAX, NOS and the like, tumour-suppressor genes: p53, Rb, Rap1A, DCC, k-rev and the like (WO94/24297), genes encoding factors involved in coagulation: factors VII, VIII, IX, suicide genes: TK and the like, natural or artificial immunoglobulins: Fab, ScFv (WO94/29446), anti-apoptotic genes: AKT and the like.

The therapeutic gene may also be an antisense gene or sequence whose expression in the target cell makes it possible to control the expression of genes or the transcription of cellular mRNAs. Such sequences may, for example, be transcribed, in the target cell, into RNAs complementary to cellular mRNAs and thus block their translation into protein, according to the technique described in Patent Application EP 140 308.

Likewise, the present invention applies to the recombinant adenoviral vectors allowing the production of retroviruses [Tumor Targetting, 3, 59 (1998)], to the adenoviruses containing one or more modifications in one or more constituent proteins of the viral capsid, in particular the fibre (protein IV) and the hexon protein (protein II), or to the fibre-free adenoviruses [Journal of Virology, 73, 1601 (1999)], each of these modifications having been introduced with the aim of modifying the natural tropism of the adenovirus [Current Opinion in Biotechnology, 8, 583 (1997)].

Moreover, the compositions according to the invention are particularly advantageous because they can be used for the preparation of a medicament intended for a therapeutic or prophylactic treatment by gene therapy.

The infectious viruses have numerous applications among which there may be mentioned their use in the field of vaccination and in the field of gene therapy. In these applications, after transferring their genetic material (RNA or DNA) into the host cell, the viruses use the cellular machinery of the infected cell to carry out the synthesis of proteins encoded by their own genome, and thus induce the specific biological effect sought. In gene therapy applications, infectious recombinant viruses carrying a therapeutic gene of interest are used to transfer this gene into specific cells of the organ of the patient to be treated. A wide variety of therapeutic protocols have been described and are currently being clinically evaluated for transferring and expressing therapeutic genes with the aid of viral vectors. Among these vectors, the nonrepetitive adenoviral vectors have been widely developed during the past few years for transferring genes encoding therapeutic proteins. Among these genes, there may be mentioned the tumour suppressor gene p53, which is involved in the control of cell proliferation. Various clinical trial protocols for transferring the p53 gene with the aid of adenoviruses in humans are currently being developed in anticancer indications. Among the other applications being developed, there may be mentioned the case of the treatment of cystic fibrosis.

The use of adenoviral vectors as therapeutic agents can only be envisaged if methods are available which make it possible to preserve and store the preparations for sufficiently long periods without significant loss of infectivity of the viruses in question. That is why the present invention is particularly of interest.

The following examples, given with no limitation being implied, show how the invention can be carried out in practice, as well as the stability of the compositions and the infectivity of the particles thus formulated.

EXAMPLE 1

Preparation of a Composition According to the Invention:

A viral suspension is prepared in the following manner: the 293 cells are cultured in a CellCube (Costar) in a DMEM medium supplemented with 10% foetal calf serum. When they reach confluence, the cells are infected at a multiplicity of infection of 2 with an aliquot from the working library of the adenovirus expressing the p53 gene. Five days after the infection, the production supernatant is harvested by draining and clarified by passing through a set of filters of decreasing porosity 10/1/0.8–0.2 μm. This supernatant is then concentrated 20 fold in volume by tangential ultrafiltration on a Millipore membrane having a cut-off of 300 kDa. The virus is then purified by chromatography on a Source 15Q column equilibrated and eluted with a sodium chloride gradient in 20 mM Tris/HCl buffer, pH 8.0. The virus peak is collected, the virus is concentrated by tangential ultrafiltration on a Millipore membrane having a cut-off of 300 kDa. The viral preparations thus obtained are of a very high purity and contain <50 ng of serum bovine albumin and <10 ng of host cell DNA for 1E12 viral particles. The virus is then formulated in the various buffers selected. To carry out this operation, the change of buffer is made by chromatography on a PD-10 column (Amersham-Pharmacia Biotech) filled with Sephadex G-25 equilibrated and eluted with the buffer selected following the supplier's instructions. After assay by chromatography, the concentration of the virus is adjusted if necessary to the target value by diluting in the selected formulation buffer. The viral stability in the various formulations is then studied by placing, for each of the formulations selected, 2 ml of viral suspension in a polypropylene tube at the temperature studied (−20° C., +4° C. or +20° C.). The samples are then preserved at this temperature for a defined period for each of the experiments in question (see examples below).

The analyses by electron microscopy are carried out by depositing the solution to be analysed on a carbon grid which is then treated by negative staining with 1.5% uranyl acetate. The apparatus used for these analyses is a Jeol 1010 electron microscope operating at a voltage of 50 kV to 100 kV.

The analyses of the size distribution of the viral particles are carried out by photon correlation spectroscopy (PCS) with the aid of a Coulter N4+ apparatus (Coultronics).

The HPLC analyses (high-performance liquid chromatography), which make it possible to quantify the viral particles, are carried out as described below: a chromatography column filled with about 1 ml of Q Sepharose® XL (45–165 μm; Amersham Pharmacia Biotech) is prepared in an HR 5/5 type column (Amersham-Pharmacie Biotech). This column, mounted on an HPLC system equipped with a UV/visible detection system operating in a 200–300 nm absorbance range, is used for the separation and the quantification of the viral particles. Before each analysis, the column is equilibrated at 30° C. in a 20 mM Tris/HCl buffer, pH 7.5 at a flow rate of 1.5 ml/min. The sample to be analysed, containing the viral particles, is injected into the column. After the injection, the column is washed with 5 volumes of the same buffer, and the bound species are eluted with a linear gradient of 0 to 1 M sodium chloride in the 20 mM Tris/HCl buffer, pH 7.5 over 30 column volumes. At the end of the gradient, the column is washed with 2 column volumes of 0.5 N sodium hydroxide before reequilibration for the next analysis. A standard curve at 260 nm is constructed with a purified preparation of adenovirus particles by chromatography. This standard preparation is titrated beforehand with respect to the particles by its absorbance at 260 nm in a 0.1% SDS solution using the conversion factor of $1\times10^{10}$ particles per unit of absorbance at 260 nm). The samples are filtered through a filter (0.22 μm) before the analysis by chromatography.

The technique for titration of the adenoviruses is described by F. L. Graham et al., Molecular Biotechnology, 3, 207 (1995). The technique for measuring the expression of the penton protein by immunotitration followed by quantification by flow cytometry is described in Boyle et al. "Determination of adenoviral vector activity using an immunotitration method", poster presented at the "5th annual meeting of viral vector and vaccines, (1998)".

EXAMPLE 2

Preservation at +4° C. of Compositions According to the Invention; Physical Stability of the Viral Particles:

The table below shows the results obtained as a function of the nature of the buffer solution and the physical stability of the vi-ral particles determined by chromatographic analysis of the preparations:

|  | Initial concentration | Viral concentration at the time considered (in days) ($\times 10^{12}$ vp/ml) | | | | | |
|---|---|---|---|---|---|---|---|
|  | ($\times 10^{12}$ vp/ml) | 10 | 15 | 20 | 35 | 60 | 90 |
| Formulation |  |  |  |  |  |  |  |
| *Tris/HCl + glycerol 10% | 8.9 | 9.8 |  |  | 9.7 | 10.1 | 10.2 |
| *Tris/HCl + glycerol 10% + Pluronic F68 10% | 8.3 | 9.0 |  |  | 8.4 | 9.0 | 8.9 |
| *Tris/HCl + glycerol 10% + PEG 400 10% | 6.6 | 7.2 |  |  | 7.2 | 6.9 |  |
| *Tris/HCl + glycerol 10% + PEG 8000 10% | 7.5 | 8.0 |  |  | 8.2 | 8.6 | 8.0 |
| *Tris/HCl + glycerol 10% + sucrose 5% | 7.4 |  | 7.7 |  | 8.5 | 7.9 | 8.5 |
| L-Lysine [20 mM, pH = 8.4] + glycerol 10% | 8.7 | 10.3 |  |  | 9.2 |  |  |
| Comparison |  |  |  |  |  |  |  |
| *Tris/HCl + sucrose 5% | 6.3 |  |  | 5.7 | 1.9 | 0.015 |  |
| *Tris/HCl + sucrose 10% | 10.5 | 8.4 |  | 0.7 |  |  |  |

*Tris/HCl: 20 mM; pH = 8.4 – % glycerol: vol/vol – % sucrose: vol/vol

EXAMPLE 3

Preservation at +4° C. of Compositions According to the Invention; Effect of the Glycerol Concentration:

The table below shows the results obtained as a function of the glycerol concentration in the formulation and gives the physical stability of the viral particles determined by chromatographic analysis of the preparations:

stabilizing adehoviral particles at. high concentration (6.9× $10^{12}$ vp/ml), the viral concentration decreases rapidly from the 2nd month.

EXAMPLE 4

Infectivity of the Adenoviruses Preserved According to the Invention at +4 or +20° C.:

|  | Viral concentration ($\times 10^{12}$ vp/ml) at the time considered | | | | | | | | |
|---|---|---|---|---|---|---|---|---|---|
|  | 0 | 15 days | 1 month | 2 months | 3 months | 4.5 months | 6 months | 9 months | 12 months |
| Formulation |  |  |  |  |  |  |  |  |  |
| *Tris/HCl + glycerol 10% (vol/vol) | 6.7 | 7.9 | 8.2 | 7.8 | 8.4 | 7.5 | 6.0 | 0.3 | — |
| *Tris/HCl + glycerol 15% (vol/vol) | 5.8 | 6.7 | 6.8 | 6.9 | 6.8 | 6.3 | 5.8 | 6.4 | 5.9 |
| *Tris/HCl + glycerol 20% (vol/vol) | 5.4 | 6.3 | 6.5 | 6.4 | 7.1 | 6.0 | 5.8 | 6.0 | 5.9 |
| *Tris/HCl + glycerol 25% (vol/vol) | 5.7 | 6.5 | 6.6 | 6.6 | 7.1 | 6.5 | 6.2 | 6.4 | 6.4 |
| Comparison |  |  |  |  |  |  |  |  |  |
| Tris/HCl 10 mM + MgCl$_2$ 1 mM + glycerol 10% (vol/vol) | 11.8 | 10.4 | 0.9 | — | — | — | — | — | — |
| Tris/HCl 10 mM + MgCl$_2$ 1 mM + NaCl 150 mM + glycerol 10% (vol/vol) | 10.3 | 5.0 | 0.8 | — | — | — | — | — | — |
| Tris/HCl 10 mM + MgCl$_2$ 1 mM + sucrose 1 M | 6.9 | 7.7 | 7.6 | 5.9 | 0.58 | 0.47 | 0.15 | 0.25 | — |

*Tris/HCl: 20 mM, pH = 8.4

The results presented in the table above clearly confirm that a content of 10% (vol/vol) is effective for the physical stabilization of the particles over a period of at least 6 months. The efficacy is also confirmed over a period of at least 1 year for the formulations including more than 10% glycerol. None of the formulations previously known provided stabilization over such a prolonged period: in particular, the formulation comprising 10 mM Tris/HCl+1 mM MgCl$_2$+1 M sucrose does not prove to be appropriate for The infectivity of the viral particles is measured by the capacity of the particles to express the transgene which they contain and to lead to the expression of the corresponding protein. The protein is here the penton protein (protein III) which is detected by immunotitration using a method of labelling with an antibody (anti-penton) followed by flow cytometry analysis. The result obtained is expressed in infectious units per ml of solution (IU/ml). The calculation of the vp/IU ratio represents a second way of expressing the variation of the infectious titre over time. Under the experimental conditions used, this ratio has a value of about 20±10 for a viral preparation freshly obtained before preserving.

The table below shows the infectivity of the particles formulated in glycerol or in sucrose after 6 or 12 months of preservation at +4° C. or after 1 month of preservation at +4° C. and then 3.5 months of preservation at +20° C.

| | Initial titre | Titre after 12 months at +4° C. | | | Titre after 6 months at +4° C. | | | Titre after 1 month at +4° C. and then 3.5 months at +20° C. | | |
|---|---|---|---|---|---|---|---|---|---|---|
| | vp/ml ($\times 10^{12}$) | vp/ml ($\times 10^{12}$) | IU/ml ($\times 10^{11}$) | vp/IU | vp/ml ($\times 10^{12}$) | IU/ml ($\times 10^{11}$) | vp/IU | vp/ml ($\times 10^{12}$) | IU/ml ($\times 10^{11}$) | vp/IU |
| Formulation | | | | | | | | | | |
| *Tris/HCl + 10% glycerol | 6.7 | | | | 6.0 | 3.0 | 20 | 4.2 | 1.1 | 38 |
| *Tris/HCl + 15% glycerol | 5.8 | 5.9 | 6.2 | 9.5 | 5.8 | 4.1 | 14 | 5.3 | 1.4 | 38 |
| *Tris/HCl + 20% glycerol | 5.4 | 5.9 | 4.5 | 13 | 5.8 | 4.6 | 13 | 5.4 | 1.4 | 39 |
| *Tris/HCl + 25% glycerol | 5.7 | 6.4 | 7.4 | 8.6 | 6.2 | 5.0 | 12 | 6.1 | 1.8 | 34 |
| Comparison | | | | | | | | | | |
| 10 mM Tris/HCl + 1 mM MgCl$_2$ + 1 M sucrose | 6.9 | — | — | — | 0.15 | <0.004 | >375 | 1.0 | 0.08 | 125 |
| 10 mM Tris/HCl + 1 mM MgCl$_2$ + 1 M sucrose | 0.36 | 0.33 | 0.33 | 10 | 0.30 | 0.36 | 9 | 0.32 | <0.004 | >800 |

*Tris/HCl: 20 mM, pH = 8.4

This study shows that the viral activity is articularly well preserved at +4° C. for all the glycerol concentrations equal to or greater than 10% and even more especially for all the glycerol concentrations equal to or greater than 15%. Likewise, the preparations preserved for 1 month at +4° C. and then for 3.5 months at +20° C. and containing at least 10% glycerol preserved their infectious capacity. The possibility of long-term preservation and at room temperature of highly concentrated adenoviral preparations is demonstrated for the first time. The formulation for comparison containing sucrose and magnesium chloride does not allow the preservation of the concentrated virus (6.9×10$^{12}$ vp/ml) either at +4° C. or at +20° C. The titre of the formulation at low concentration (0.36×10$^{12}$ vp/ml) decreases after a preservation of 1 month at +4° C. followed by a preservation of 3.5 months at +20° C. Formulations containing sucrose are totally unsuitable when the concentration is increased.

After three months of preservation, the various preparations were analysed by electron microscopy. These analyses show that: at a glycerol concentration of 20%, the particles appear native, filled, complete and symmetrical. Practically no free subunit is detectable in the medium. On the other hand, in the formulation for comparison at a high viral concentration, most of the particles have aggregated either into masses containing about 50 particles, or into filamentous structures. Some particles have lost part of their capsomers and have a more rounded or ovoid structure. The capsomers and the fibres released into the medium remain completely dispersed and can be very easily observed. This is observed both at +4° C. and at +20° C. After 12 months at 4° C., the particles preserved in 20% of glycerol appear unchanged (filled, complete and symmetrical).

EXAMPLE 5

Infectivity of an Adenoviral Preparation Formulated in Tris/HCl+Glycerol and Preserved at −20° C.:

In this example, the infectivity of the particles is determined by titration in pfu/ml. The term pfu ("plaque forming unit") corresponds to the determination of the infectivity of an adenovirus solution. This determination is carried out by infecting an appropriate cell culture, and measuring, generally after 15 days of incubation, the number of plaques of infected cells. These assays are based on biological methods and the values obtained are to a certain extent dependent on the operating conditions used [J. Virol., 70, 7498 (1996)].

The table below shows the infectious titre, measured in a pfu test, of a viral preparation preserved for 2 months at −20° C.

| Formulation | Initial titre vp/ml ($\times 10^2$) | Titre at D60 vp/ml ($\times 10^{12}$) | Titre at D60 pfu/ml ($\times 10^{11}$) | vp/pfu ratio at D60 |
|---|---|---|---|---|
| 20 mM Tris/HCl (pH 8.4) + 10% glycerol | 7.7 | 7.7 | 3.0 | 26 |

The value for the measurement of the infectious titre, and more particularly the vp/pfu ratio indicate that the viral particles have not been impaired by the freezing-thawing step or by the preservation for 2 months at −20° C. (This ratio has a value of about 20 to 30 for the initial viral preparation).

EXAMPLE 6

Preservation at +4° C. of Compositions According to the Invention; Physical Stability of the Viral Particles:

The table below shows the results obtained as a function of the nature of the buffer solution and the physical stability of the viral particles determined by chromatographic analysis of the preparations:

| Formulation | Initial concentration ($\times 10^{12}$ vp/ml) | Viral concentration at the time considered (in days) ($\times 10^{12}$ vp/ml) | | |
|---|---|---|---|---|
| | | 30 | 60 | 90 |
| 20 mM Tris/HCl (pH 8.4) + glycerol 20% | 29.2 | 31.4 | 32.1 | 33.7 |
| 100 mM Tris/HCl (pH 8.4) + glycerol 20% | 7.7 | 8.4 | 6.0 | 8.3 |
| 20 mM Tris/HCl (pH 8.4) + glycerol 20% + ethanol 10% | 13.9 | 14.8 | 14.7 | 15.0 |
| 20 mM Lysine/HCl (pH 8.4) + glycerol 20% | 7.8 | 8.4 | 6.8 | 7.7 |
| 20 mM Hepes/Na (pH 8.4) + glycerol 20% | 7.9 | 8.4 | 7.0 | 8.6 |

EXAMPLE 7

Preservation at +4EC of Compositions According to the Invention; Effect of the PH of the Buffer Solutions:

The table below shows the effect of the pH of the buffer solution on the infectivity of the particles formulated in 20 mM Tris, 10% glycerol, after 3 months of preservation:

| 20 mM Tris/HCl + 10% glycerol formulation | titre ($\times 10^{12}$ vp/ml) | Titre after 3 months Initial at +4° C. | | |
|---|---|---|---|---|
| | | vp/ml ($\times 10^{12}$) | IU/ml ($\times 10^{11}$) | vp/IU |
| pH = 7.5 | 3.1 | 2.5 | 0.18 | 136 |
| pH = 8.0 | 6.7 | 6.1 | 1.1 | 56 |
| pH = 8.5 | 7.2 | 7.0 | 1.6 | 44 |
| pH = 9.0 | 6.4 | 5.8 | 1.2 | 48 |
| pH = 9.5 | 6.0 | 5.5 | 2.0 | 28 |

This study shows that the viral activity is particularly well preserved at +4° C. in the 20 mM Tris/HCl formulations containing 10% glycerol at pH values ranging from 8.0 to 9.5.

Below pH=8.0, stability is no longer maintained at +4° C.

The invention claimed is:

1. A composition comprising adenovirus, a Tris/HCl buffer solution, and glycerol, wherein said buffer solution does not contain added divalent metal cations or alkali metal cations, and wherein the buffer solution maintains the pH of said composition at a pH ranging from 8.0 to 9.6.

2. The composition according to claim 1, wherein said composition is stored at a temperature of up to 20° C.

3. The composition according to claim 1, wherein said composition is stored at a temperature ranging from 4° C. to 20° C.

4. The composition according to claim 1, wherein the buffer solution maintains the pH of said composition at a pH ranging from 8.4 to 8.8.

5. The composition according to claim 1, further comprising an adjuvant.

6. The composition according to claim 5, wherein the adjuvant is a polymer, sugar, or alcohol.

7. The composition according to claim 6, wherein the adjuvant is a polymer chosen from a polyethylene glycol, a pluronic, or a polysorbate.

8. The composition according to claim 6, wherein the adjuvant is a sugar chosen from sucrose, dextrose, or mannitol.

9. The composition according to claim 6, wherein the adjuvant is ethanol.

10. A composition comprising adenovirus, a Tris/HCl buffer solution, and glycerol, wherein said buffer solution does not contain added divalent metal cations or alkali metal cations, and wherein the molar concentration of the Tris/HCl buffer solution is 20 mM.

* * * * *